(12) United States Patent
Xue et al.

(10) Patent No.: US 8,313,741 B2
(45) Date of Patent: Nov. 20, 2012

(54) USE OF MEDULLIADRENAL CHROMAFFIN CELLS OR PEPTIDE FUNCTIONAL CELLS

(75) Inventors: Yilong Xue, Beijing (CN); Guanghua Liu, Beijing (CN)

(73) Assignee: Yilong Xue, Beijing (CN)

( * ) Notice: Subject to any disclaimer, the term of this patent is extended or adjusted under 35 U.S.C. 154(b) by 591 days.

(21) Appl. No.: 11/576,061

(22) PCT Filed: Sep. 27, 2004

(86) PCT No.: PCT/CN2004/001104
§ 371 (c)(1),
(2), (4) Date: Nov. 1, 2007

(87) PCT Pub. No.: WO2006/034601
PCT Pub. Date: Apr. 6, 2006

(65) Prior Publication Data
US 2008/0187521 A1 Aug. 7, 2008

(51) Int. Cl.
*A61K 35/12* (2006.01)
*C12N 5/06* (2006.01)
*A61P 25/30* (2006.01)
*A61P 25/36* (2006.01)

(52) U.S. Cl. ..................... 424/93.21; 435/325

(58) Field of Classification Search .................. None
See application file for complete search history.

(56) References Cited

FOREIGN PATENT DOCUMENTS
CN 1127948 11/2003
EP 0547203 * 8/1997

OTHER PUBLICATIONS

Wu et al: "Implantation of AtT-20 or Genetically Modified AtT-20/hENK Cells in Mouse Spinal Cord Induced Antinociception and Opioid Tolerance." The Journal of Neuroscience. Aug. 1994; 14(8): 4806-4814.*
Wu et al (Journal of Neuroscience. 1994; 14(8): 4806-4814).*
Wang et al (Neuropharmacology, May 1994; 33(5): 681-692).*
Czech et al (Progress in Neurobiology. 1995; 46: 507-529).*
A.M. Sun, "Microencapsulation of Pancreatic islet cells: a bioartificial endocrine pancreas." Methods Enzymol., 1988; 137: 575-580.

* cited by examiner

*Primary Examiner* — Scott Long
(74) *Attorney, Agent, or Firm* — Ladas & Parry LLP

(57) ABSTRACT

The present invention relates to new use of medulliadrenal chromaffin cells or opioid-peptidergic cells, in particular to their use for treating and/or relieving withdrawal syndrome resulting from drug addiction or drug abuse.

1 Claim, No Drawings

USE OF MEDULLIADRENAL CHROMAFFIN CELLS OR PEPTIDE FUNCTIONAL CELLS

TECHNICAL FIELD

The present invention relates to new use of medulliadrenal chromaffin cells or opioid-peptidergic cells, in particular to their use for treating and/or relieving withdrawal syndrome resulting from drug addiction or drug abuse.

BACKGROUND ART

Drug dependence and addiction caused by drug-taking and drug abuse have become an increasingly serious social problem. Common therapies include substitution and gradual withdrawal therapy (such as Methadone and Dihydroetorphine etc), subhibernation therapy, Chinese medicine therapy and the like. However, there is no accepted and ideal method available up to date.

Currently the mechanism underlying addiction to opioids is believed to be related to the function of opioid receptors. Under normal physiological conditions, opioid receptors are subjected to the action of certain basal level of endogenous opioid peptides (EOP). When exogenous opioid compounds (EOC) such as morphine are given, morphine will occupy the rest of opioid receptors, thereby enhancing the analgesic effects of endogenous opioid peptides. When exogenous morphine is given successively and in excess, the release of EOP from EOP neurons will decrease sharply through feedback regulation, and more exogenous morphine will be needed to maintain the analgesic effects. Therefore, once drugs such as morphine are stopped, neither endogenous opioid peptides nor exogenous morphine is available to act on opioid receptors, and a series of abnormal symptoms due to increased secretion of other neurotransmitters will appear, clinically known as withdrawl syndrome.

Normal organisms have cells that can secret endogenous opioid peptides, such as medulliadrenal chromaffin cells (MCCs) and the like. MCC can secret three types of substances: monoamines, such as norepinephrine (NE), epinephrine (E), dopamine and the like; endogenous opioid peptides, such as leucine-enkephalin, methionine-enkephalin, dynorphin and the like; and various growth factors, such as nerve growth factor, epidermal growth factor and the like. MCC, upon relevant stimulations, can secret corresponding substances, producing stress and analgesic effects. In the beginning of 1980's, two research groups from USA and Switzerland tried to implant homogenous (human, rat) adrenal medulla tissues and chromaffin cells into subarchnoid space of spinal cord for treating pain and had finally obtained satisfactory results. Because of the rare sources of human adrenal medulla tissues and chromaffin cells, in 1990's, the research group from USA had tried to implant heterogeneous bovine adrenal medulla chromaffin cells (hereafter abbreviated as BCCs) into subarachnoid space of cancer patients to cure pain. In order to overcome the immune rejection, they used polyacrylamide hollow fiber tube of 5 cm in length and 1 mm in diameter to coat BCCs. As said hollow fiber tube only allow small molecules to pass through, the secretion of BCCs can diffuse slowly and uniformly out of the fiber tube to exert the analgesic effect, while macromolecular immunoglobulin in host body cannot pass through the hole of tube wall, so that the cells can survive in host body for a long period (about 1 year) and allows continuous delivery of analgesic substances to treat the patients suffering from pain. But the hollow fiber tube has a large volume. On one side, the dead volume of tube affect the dispersion of nutrients and metabolites, which make the cells inside tube can't survive chronically. On the other hand, implantation of fiber tube with large volume into subarachnoid space would stimulate and oppress spinoneure, thereby cause many undesirable side effects. Moreover, as the volume of hollow fiber tube is large, it must to be implanted into subarachnoid space by surgical operation, which would injure patient more or less. In the meantime, the hollow fiber tube made of materials such as chitosan, polyacrylamide and sodium carboxymethylcellulose (used in USA) has poor tissue biocompatibility, which causes tissue reaction in host body. On the other side, the microcapsules with three layer membrane structure of sodium alginate-polylysine-sodium alginate (hereafter APA microcapsule) have little volume (200-1000 μm in diameter) and high biocompatibility, which facilitates the long intact presence of the microcapsule in host cell and the long survival of the cells inside microcapsule. The experiments have indicated that microcapsule membrane can cut off macromolecule with molecular weight beyond 110,000 Kd (dalton), prevent immunoglobulin and immunological competent cells pass through said membrane into microcapsule to destroy the animal cells inside, which thus provide proper immune protection. Experiments also indicated that APA microcapsules have proper biocompatibility, and have long term existence (about one year and half) in small or big animal body. The research on implantation of islands of Langerhans, liver cells, parathyroid and genetic recombinant growth-hormone secretory cells for treating disease model animal have provided the evidence that said APA microcapsule protect heterogeneous implant from host immune system. However, so far, there is no report worldwide about use of APA microencapsulated bovine medulliadrenal chromaffin cells for treating and/or relieving withdrawl syndrome.

DESCRIPTION OF THE INVENTION

The object of the present invention is to provide a product suitable for treating or relieving withdrawl syndrome from addiction, with high biocompatibility, long duration of action, few tbovineic side effects and easy to manipulate.

The inventors now have found that medulliadrenal chromaffin cells or opioid-peptidergic cells obtained for example by genetic engineering, in particular APA microencapsulated bovine medulliadrenal chromaffin cells, have good treating or relieving effect on withdraw syndrome from addiction. The present invention is made based on said finding.

In a first aspect, the present invention relates to use of medulliadrenal chromaffin cells or opioid-peptidergic cells in the manufacture of a product for treating and/or relieving withdrawl syndrome resulting from drug addiction or abuse.

In another aspect, the present invention relates to a method for treating and/or relieving withdrawl syndrome resulting from drug addiction or abuse, comprising administering by injection to a drug addict or abuser medulliadrenal chromaffin cells or opioid-peptidergic cells.

In a further aspect, the present invention relates to a product for treating or relieving withdrawl syndrome, comprising medulliadrenal chromaffin cells or opioid-peptidergic cells, in particular APA microencapsulated medulliadrenal chromaffin cells.

In yet another aspect, the present invention relates to a medicine of microencapsulated bovine medulliadrenal chromaffin cells or opioid-peptidergic cells for treating or relieving withdrawl syndrome, characterized in that said medicine is prepared by the following steps:

(1) mixing the bovine medulliadrenal chromaffin cells or opioid-peptidergic cells with a sodium alginate solution of 10-20 g/L to form a suspension, said suspension containing $0.1-1\times10^{10}$ cells per liter;

(2) dispersing the suspension of step (1) into a calcium chloride or calcium lactate solution of 80-120 mmol/L, in the form of droplets of 150-1000 μm in diameter using a spraying device, the two liquids being in such a proportion that the resulting mixture contains $0.1-1\times10^8$ cells per liter, leaving to stand for 5-20 minutes, discarding the supernatant after complete precipitation, to obtain the calcium alginate bead precipitates comprising bovine medulliadrenal chromaffin cells;

(3) adding the precipitates from step (2) into a polylysine solution of 0.3-0.7 g/L in such a proportion that the resulting mixture contains $0.2-2\times10^8$ cells per liter, mixing thoroughly, leaving to stand for 5-20 minutes, discarding the supernatant after complete precipitation, to obtain the precipitates;

(4) adding the precipitates from step (3) into a sodium alginate solution of 1.0-2.0 g/L in such a proportion that the resulting mixture contains $0.2-2\times10^8$ cells per liter, mixing thoroughly, leaving to stand for 3-15 minutes, discarding the supernatant after complete precipitation, to obtain the precipitates;

(5) adding the precipitates from step (4) into a sodium citrate solution of 40-70 mmol/L in such a proportion that the resulting mixture contains $0.2-2\times10^8$ cells per liter, mixing thoroughly, leaving to stand for 5-20 minutes, discarding the supernatant after complete precipitation, to obtain the precipitates of microencapsulated bovine medulliadrenal chromaffin cells or opioid-peptidergic cells;

(6) washing the precipitates from step (5) by adding them into a sodium chloride solution of 9 g/L, finally transferring the precipitates into a cell culture, culturing and storing as a medicine of microencapsulated bovine medulliadrenal chromaffin cells or opioid-peptidergic cells.

According to the present invention, the medulliadrenal chromaffin cells can be derived from a mammal, such as human, cattle, sheep, pig, rat or mouse, or can be genetically engineered cells, preferably bovine medulliadrenal chromaffin cells.

According to the present invention, the medulliadrenal chromaffin cells or opioid-peptidergic cells are used in microencapsulated form. APA microencapsulated bovine medulliadrenal chromaffin cells are preferred.

In a further embodiment, the microencapsulated bovine medulliadrenal chromaffin cells used in the present invention preferably have a purity of at least 80%.

According to the present invention, the opioid-peptidergic cells are for example cells capable of secreting opioid peptides obtained by modification of mammal such as human or bovine medulliadrenal chromaffin cells by genetic engineering.

In the preparation of the medicine of microencapsulated bovine medulliadrenal chromaffin cells according to the present invention, it is preferred in step (2) to disperse the suspension from step (1) in droplets of 180 to 500 μm in diameter.

As for use, the injection of the APA-microencapsulated BCCs ($2-9\times10^6$ cells) according to the present invention into subarachnoid space of patients suffering from withdrawl syndrome will produce therapeutic effect within 4-24 hours, and one injection may maintain therapeutic effects for over 9 months.

In particular, said bovine medulliadrenal chromaffin cells (BCCs) of the present invention refers to the cells in bovine adrenal medulla capable of being stained with chromium-containing dye or opioid-peptidergic cells obtained by modification by genetic engineering, which can secrete monamines, enkephalins (including methionine-enkephalin (MEK), leucine-enkephalin), neurotrophic factors and the like.

The acquisition and purification of BCC can be carried out using methods known in the art. For example, it may be carried out by reacting bovine adrenal with collagenase to decompose the collagen tissue, then separating bovine adrenal tissue into single cells by mechanical method, followed by filtration through screens of 170 mesh (88 μm), with bovine adrenal medulla cells (containing chromaffin cells, endothelial cells, fibroblasts and blood cells) passing through the filter screen. The filtrate is centrifuged and the supernatant is discarded, to give the aforesaid bovine adrenal medulla cell pellet, in which the chromaffin cells comprise about 50-60% of total cells, endothelial cells and fibroblasts comprise about 40-50% of total cells. Since blood cells are small, usually they are not included in the total cells. Notably, as the BCCs account for about 50-60% of the total number of bovine adrenal medulla cells, they can be used in the present invention even without further purification. However, in order to improve the therapeutic effect, it is preferably purified to a purity of at least 80%. The purification methods, for example, conventional wall-attaching purification method which is based on the distinct attachment tendency of different cells can be used. For example, culture mixture which contains chromaffin cells, endothelial cells, fibroblasts and blood cells are cultured in culture-flask for hours, most of fibroblasts attach the wall, while chromaffin cells, endothelial cells and blood cells don't attach to wall, thus most fibroblasts can be removed through changing bottle. For the blood cells can't grow on wall, so most of blood cells can be removed through culturing them for longer time (for example 24-28 hours) and changing bottles again after the chromaffin cells and endothelial cells being attached to wall. After changing bottle 2 times, the purity of BCC can arrive at 80% of total cells (except the blood-cell).

As for the methods of cell counting, conventional counting process of observing under microscope after staining can be used, such as "Trypan blue stain" (see "Tissue Culture Media and Reagents", page 1566).

In the preparation of the medicine of microencapsulated medulliadrenal chromaffin cells or opioid-peptidergic cells obtained by e.g. genetic engineering according to the present invention, the amount of solution used in each step may be determined depending on cell numbers defined. For example, in the preparation of the medicine of the present invention as described above, 1 liter suspension derived from step (1) contains $0.1\times10^{10}$ cells, while 1 liter mixture from step (2) contains $0.1\times10^8$ cells. That is to say, cell concentration of suspension from step (1) is about 100 times of that from step (2), thus, it is preferable to disperse 1 ml suspension from step (1) into 100 ml calcium chloride solution of step (2). The same applies to other steps.

The aim of forming calcium alginate bead in step (2) is to create a condition for gaining microcapsules containing bovine medulliadrenal chromaffin cells in step (5). In step (5), sodium ion of sodium citrate replaces the calcium ion of calcium alginate bead to form many microcapsules with small hole. Those microcapsules contain a large number of BCCs, and BCCs are encapsulated by sodium alginate.

There is no specific limit on the methods of forming calcium alginate bead, it is only required that the sodium alginate suspension containing BCCs can disperse into the solution of calcium chloride in adequately tiny liquid droplets. The diameter of said droplets of suspension of sodium alginate is usually in the range of 150-1000 μm, preferably in the range of 180-500 μm. If the diameter of the micro-drops is more than 1000 μm, the resulting microcapsules will be too large so that it will burst easily when being injected into animal or human body, which is undesirable. Liquid-droplet dispersion methods usually include pinhead injection method, nebulization and so on, and nebulization is preferred. The most preferred method is to spray by electrostatic droplet generator such as one manufactured by Toronto University, Canada (see SUN, A.M. Micro-encapsulation of pancreatic islet cell: a bio-artificial endocrine pancreas In Methods in Enzymology, Vol. 137, page 575-580, 1988).

The embodiments of the present invention have been explained in detail. Those skilled in the art will readily understand the present invention upon reading the description and the following examples.

As compared to the prior art, the present invention has the following positive effects:

Animal experiments have shown that the APA microencapsulated medulliadrenal chromaffin cells or opioid-peptidergic cells obtained e.g. by genetic engineering according to the present invention can result in release of endogenous opioids in small amounts over a long period to act upon the opioid receptors in the patients. The implanted cells will serve as a "mini biologic pump" for a continuous secretion in small amounts. Over time, the clinical withdrawl symptoms will be alleviated, and at the same time the negative feedback inhibition of the endogenous secretion by opioid-peptidergic cells in the patient will be reduced, allowing their capability to secret EOP to restore, thus achieving abstinence.

The present invention has the following features as compared to the prior art:
1. APA microcapsules according to the present invention have a small volume (180 to 500 μm in diameter), which thus have at least three advantages, (1) it accelerate diffusion of nutrients and metabolites, thus the cells inside the capsules can survive for a long period; (2) it is not necessary to implant hollow fiber tube surgically, and the microcapsules may be injected into subarachnoid space only by conventional lumbar puncture, with little tissue damage; (3) located in the subarachnoid space, it has few side effects such as stimulation and compression to the spinal nerves;
2. As compared to immune isolation membranes made of other material, APA microcapsules have good biocompatibility;
3. Lots of experiments have demonstrated that the APA microcapsules of the present invention provide excellent immunity protection.
4. The BCCs can secrete substances antagonizing withdrawl syndrome continuously (for over 3 months) in the subject to provide sustained treatment and/or relieve of withdrawl syndrome;
5. Microencapsulated BCCs can act to treat and/or relieve withdraw syndrome in the subject for a long period;
6. As compared to human medulliadrenal chromaffin cells, bovine medulliadrenal chromaffin cells can be obtained in large amounts;
7. Microencapsulated BCCs may be stored under low temperature, thus facilitating long-range transport and bulk supply.

MODE OF CARRYING OUT THE INVENTION

The present invention will be further illustrated by the following examples, experiments and applications, which are not intended to limit the scope of the present invention in any way.

Example 1

Isolation and Purification of BCCs 1. 12 fresh bovine adrenal glands were obtained from a shambles (time of lack of blood supply under room temperature less than 1 hour) and were transported immediately to the laboratory under cold storage.
2. A collagenase I solution of 1 g/L was injected through the vein into the adrenal gland (5 ml per gland), and the glands were left to stand at 37° C. for 30 min to allow thorough reaction between the collagense and the connective tissues surrounding the bovine adrenal cells.
3. The adrenal cortex was cut longitudinally, and the medulla was isolated and cut into small pieces.
4. 60 ml of a collagenase I solution of 1 g/L were added to the minced medulla and left to stand for another 30 min.
5. The mixture was filtered through a steel screen of 170 mesh (88 μm) and the filtrate was collected.
6. The filtrate was centrifuged and the supernatant was discarded to obtain the pellet comprising bovine medulliadrenal chromaffin cells (including BCCs, endothelial cells, fibroblasts and blood cells).
7. The cells were counted using trypan blue exclusion method, and the total number of cells (excluding blood cells) obtained was $5.8 \times 10^7$, the survival rate of cells being 90%.
8. The cells were transferred to two culture flasks, and 20 ml of DMEM (Dulbeco's Modified Eagle Medium) supplemented with 100 U/ml penicillin, 100 ug/ml streptomycin and 10 v % calf serum were added to each flask. The flasks were incubated in an incubator at 37° C. in 5 v % $CO_2$. 5 hours later, the cells were transferred to another flask and the culturing was continued until most of the BCCs become attached to the wall of flasks.

Typically the culturing takes at least 24 hours. In the preparation of medicine of microencapsulated animal cells, it is only required to remove the solution from the culture flask and harvest the BCCs by conventional trypsinization for further processing.

It is to be noted that the method as used in Example 1 is conventional and does not have any limiting effect on the present invention.

Example 2

Preparation of Microencapsulated Animal Cells

1. The BCCs obtained according to Example 1 were centrifuged, and the BCC pellet was washed and diluted by normal saline to 1 ml, which was then transferred to a centrifuge tube.
2. The cells were counted using trypan blue exclusion method, and the total number of cells obtained was $3 \times 10^6$ cells, the purity of BCCs being 82%.
3. 1 ml of a sodium alginate solution of 15 g/L was added thereto with stirring to produce a suspension.
4. The suspension was sprayed into 100 ml of a calcium chloride solution of 100 mmol/L using an electrostatic droplet generator (manufactured by Toronto University, Canada). In ten minutes, calcium alginate beads of 180 to 500 μm in diameter containing cells precipitated. Once the precipitation was complete, the supernatant was discarded.
5. The calcium alginate beads were added to 50 ml of a polylysine solution of 0.5 g/L, mixed thoroughly and left to stand at room temperature for 10 min. Once the precipitation was complete, the supernatant was discarded.
6. The precipitates obtained in step 5 were added to 60 ml of a sodium alginate solution of 1.5 g/L, mixed thoroughly and left to stand at room temperature for 10 min. Once the precipitation was complete, the supernatant was discarded.

7. The precipitates obtained in step 6 were added to 60 ml of a sodium citrate solution of 55 mmol/L, and left to stand at room temperature for 10 min. Once the precipitation was complete, the supernatant was discarded to give microencapsulated animal cells precipitates containing BCCs.

8. The precipitates were washed with a sodium chloride solution of 9 g/L, and then transferred to the DMEM medium as described in step 8 in Example 1, ready for use as injectable microencapsulated BCCs.

Experiment 1: Effects of Microencapsulated BCCs on Withdrawl Syndrome in Rats

Materials:

1. Reagents: morphine hydrochloride, Methadone, Naloxone hydrochloride, physiologic saline, NO kit, SOD kit, prostaglandin E2 RIA kit, heparin sodium injection, Indomethacin injection, chloral hydrate injection.

2. Microencapsulated chromaffin cells

3. Experimental animal: Wistar rats, weighing about 250 g.

Methods:

1. Establishment of Morphine Dependence Model in Rats (cf. the Method as Described by Ling GSF):

150 Wistar rats weighing about 250 g with equal numbers of male and female were randomly divided into 5 groups of 30 in each group. Groups 1 to 4, as morphine dependence models, received 2 subcutaneous injections of morphine (8:00 am and 6:00 pm) daily starting from a dosage of 20 mg/kg per day, with an increase of 20 mg/kg per day, for 5 days. The final dosage was 100 mg/kg per day. 4 hours after the last injection of morphine, the rats were given intraperitoneal injection of Naloxone hydrochloride at 4 mg/kg and were observed for 1 hour, recording the scores of each withdraw symptom in each group. Those rats with scores higher than 5 were considered as successful models.

2. Treatment To each Group:

16 hours after successful modeling (Day 6), each group was subjected to a different treatment.

Microencapsulation Group Each rat was implanted in the subarachnoid space $2 \times 10^5$ APA-BCCs, and the injection of morphine was stopped.

Self-withdrawl Group: Each rat was injected 20 ul of phiologic saline into the subarachnoid space and the injection of morphine was stopped.

3. Observation and Acquisition of Data:

The first challenge: On the day following the implantation (Day 7), 3 h-4 h after the last injection of morphine, the rats were injected i.p. naloxone hydrochloride at 4 mg/kg body weight and were observed for 1 hour, recording and scoring each withdrawl symptom. The body weight and the blood levels of NO, SOD and prostagladin E2 were measured.

The second challenge: 4 days after the above challenge, the rats were injected i.p. naxolone hydrochloride at 4 mg/kg for the second challenge and were observed for withdrawl symptoms.

APPENDIX 1

Scoring of Withdrawl Symptoms (cf. the Method of Ling GSF)

(1) Abnormal posture, 2; high irritability, irritation on touch, 1; irritation upon approaching, 2.
(2) Odontoprisis: intermittent, 0.5; continuous, 1. Abnormal behaviors are scored once per hour.
(3) Lacrimation: 4.
(4) Diarrhea: soft feces, 4; unshapen, 8.
(5) Sialorrhea: mild, 1; marked, 2.

Symptoms of autonomic nerve system are scored only per 15 min.

4. Data Acquisition:

The scores of withdrawl symptoms upon the first and second challenges of rats in each group were collected. The weight loss of rats in each group at different time points after challenge was compared. The changes in the blood levels of NO, SOD, PGE2 of rats in each group were recorded.

5. Statistical Analysis.

Results:

Effects of subarachnoid implantation of microencapsulated bovine chromaffin cells on morphine dependent rats Morphine dependence models were successfully established in 5 days in 10 Wistar rats weighing about 240 g (all male), with an average score of withdrawl symptoms of 24. The rats were randomly divided into 2 groups of 5 each. The first group was microencapsulation group, and the second was self-withdrawl group.

The experimental results are shown below:

TABLE 1

Comparison of scores of withdrawl symptoms of rats in each group

| Group | Scores | | |
|---|---|---|---|
| | Pretreatment | First challenge | Second challenge |
| microencapsulation group | 24 ± 0.01 | 8.1 ± 0.98 | 6.75 ± 0.25 |
| self-withdrawal group | 24 ± 0.01 | 8.9 ± 0.98 | 7.50 ± 0.29** |

**$P < 0.01$
* $P < 0.05$ vs. microencapsulation group

TABLE 2

Comparison of weight loss at different time points of rats in each group

| Group | time | | | | |
|---|---|---|---|---|---|
| | 1 h | 24 h | 48 h | 72 h | 96 h |
| microencapsulation group | 23.36 ± 3.77 | 21.9 ± 2.87 | 15.25 ± 2.74 | 15.8 ± 5.72 | 15.9 ± 5.72 |
| self-withdrawal group | 33.12 ± 5.56* | 30.2 ± 3.34** | 33.4 ± 6.21** | 27.15 ± 1.79** | 27.2 ± 1.87** |

**$P < 0.01$
*$P < 0.05$ vs. microencapsulation group

TABLE 3

Blood levels of NO, SOD at different time points after challenge of rats in each group

| Group | Biochemical indicator | | | | | |
|---|---|---|---|---|---|---|
| | NO | | | SOD | | |
| | 1 h | 48 h | 96 h | 1 h | 48 h | 96 h |
| microencapsulation group | 77.67 ± 5.48 | 107.2 ± 28.2 | 29.41 ± 8.02 | 8.01 ± 0.015 | 7.89 ± 0.018 | 7.87 ± 0.06 |
| self-withdrawal group | 64.48 ± 7.78* | 35.02 ± 15.1** | 15.85 ± 5.55* | 5.99 ± 2.2 | 7.88 ± 0.012 | 7.85 ± 0.07 |

**P < 0.01
*P < 0.05 vs. microencapsulation group

It can be seen from the above tables there are (statistically) significant differences in withdrawl symptom scores, body weight and NO level between the microencapsulation group and the self-withdrawl group. The results indicate that subarachnoid implantation of microencapsulated bovine chromaffin cells can significantly reduce withdrawl symptoms in morphine-dependent rats.

Example 3

Establishment of Immortalized Human Medulliadrenal Chromaffin Cell Line

Primary Culture of Human Medulliadrenal Chromaffin Cell:
Fresh adrenal glands from adults or fetuses free of adrenal diseases were obtained. Human medulliadrenal chromaffin cells (HCCs) were obtained by mechanical and chemical means and cultured. The biological features of the HCCs were checked for capability to secret catecholamines and enkephalins.

Establishment of Human Medulliadrenal Chromaffin Cell Line:
The eukaryotic expression plasmid PClneo-hTERT encoding hTERT and neo genes was introduced into HCCs in primary culture by liposome-mediated transfection. G418 was used to screen the positive clones. RT-PCT method was used to detect the telomerase activity of the positive clones, verifying the capability of exogenous hTERT to activate telomerase activity in the target cell. Clones that grew well in the presence of G418 were chosen, and the expression of mRNA and protein of hTERT in the positive clones was determined by RT-PCR and Western Blot, respectively.

It is to be noted that the methods as used in Example 3 are conventional and do not limit the scope of the present invention.

Example 4

Preparation of Microencapsulated Medicine of Genetically Engineered Cells

1. The HCCs as obtained according to Example 3 were trypsinized to give HCC pellets, which were wached with physiologic saline.
2. 1 ml of a sodium alginate solution of 15 g/L was added thereto to form a suspension.
3. The suspension was sprayed into 100 ml of a calcium chloride solution of 100 mmol/L using an electrostatic droplet generator to obtain calcium alginate beads of 180 to 500 μm in diameter containing cells. Once the precipitation was complete, the supernatant was discarded.
4. The calcium alginate beads were added to 50 ml of a polylysine solution of 0.5 g/L, mixed thoroughly and left to stand at room temperature for 5-10 min. Once the precipitation was complete, the supernatant was discarded.
5. The precipitates obtained in step 4 were added to 60 ml of a sodium alginate solution of 1.5 g/L, mixed thoroughly and left to stand at room temperature for 5-10 min. Once the precipitation was complete, the supernatant was discarded.
6. The precipitates obtained in step 5 were added to 60 ml of a sodium citrate solution of 55 mmol/L, and left to stand at room temperature for 5-10 min. Once the precipitation was complete, the supernatant was discarded to give microencapsulated HCC precipitates.
7. The precipitates were washed with a sodium chloride solution of 9 g/L, and then transferred to DMEM medium and cultured, ready for use as injectable microencapsulated HCCs.

Example 5

Effects of Subarachnoid Implantation of Microencapsulated HCCs on Withdrawl Syndrome in Morphine-Dependent Rats Materials and Methods: the same as those used in the Experiment 1 (Effects of microencapsulated BCCs on withdrawl syndrome in rats), except that the test agent is microencapsulated HCC (APA-HCC).

Morphine-dependence model was successfully established in a total of 10 Wistar rats weighing about 240 g (all male) in 5 days, with an average withdrawl symptom score of 24. The rats were randomly divided into 2 groups of 5, the first group being microencapsulation group, and the second being self-withdrawl group.

The experimental results showed that the withdrawl symptom score in the microencapsulation group after the second challenge was significantly lower as compared with the self-withdrawl group (p<0.01); and starting from 1 day after the implantation, the weight loss in rats of the microencapsulation group was significantly less than the self-withdrawl group (p<0.01), suggesting that subarachnoid implantation of microencapsulated HCCs can significantly reduce withdrawl symptoms in morphine-dependent rats.

What is claimed is:

1. A method for treating and/or relieving withdrawal syndrome resulting from drug addiction or abuse, comprising:
administering by injection to a drug addict or abuser APA microencapsulated medulliadrenal chromaffin cells; and
relieving withdrawal symptoms comprising reducing the loss of weight over time.

* * * * *